(12) United States Patent
Clark et al.

(10) Patent No.: US 9,791,398 B2
(45) Date of Patent: Oct. 17, 2017

(54) MEASUREMENT DEVICE WITH SENSOR ARRAY

(75) Inventors: William Clark, Wexford, PA (US); Sung Kwon Cho, Pittsburgh, PA (US); Yuejun Zhao, Pittsburgh, PA (US); Timothy J. Syciarz, Pittsburgh, PA (US); R. Maxwell Flaherty, Auburndale, FL (US); J. Christopher Flaherty, Auburndale, FL (US); David W. Wagner, Boston, MA (US)

(73) Assignee: pHase2 microtechnologies, Inc., Pittsburgh, PA (US)

( * ) Notice: Subject to any disclaimer, the term of this patent is extended or adjusted under 35 U.S.C. 154(b) by 387 days.

(21) Appl. No.: 14/343,376

(22) PCT Filed: Sep. 6, 2012
(Under 37 CFR 1.47)

(86) PCT No.: PCT/US2012/053902
§ 371 (c)(1),
(2), (4) Date: Apr. 30, 2015

(87) PCT Pub. No.: WO2013/036598
PCT Pub. Date: Mar. 14, 2013

(65) Prior Publication Data
US 2016/0003761 A1    Jan. 7, 2016

Related U.S. Application Data

(60) Provisional application No. 61/531,238, filed on Sep. 6, 2011.

(51) Int. Cl.
*G01N 27/28* (2006.01)
*G01N 27/30* (2006.01)
(Continued)

(52) U.S. Cl.
CPC ...... *G01N 27/302* (2013.01); *B01L 3/502738* (2013.01); *G01N 27/28* (2013.01);
(Continued)

(58) Field of Classification Search
CPC .... G01N 27/302; G01N 27/307; G01N 27/28; G01N 27/4035; G01N 33/4836;
(Continued)

(56) References Cited

U.S. PATENT DOCUMENTS 4,120,292 A  *  10/1978  LeBlanc, Jr.  ......  A61B 5/14539
204/403.06
5,405,510 A       4/1995  Betts et al.
(Continued)

FOREIGN PATENT DOCUMENTS

DE    102009007851 A1    8/2010
WO        0164344 A2     9/2001

OTHER PUBLICATIONS

Official Action for JP2014-528702, dated Jul. 21, 2016, 4 pages.
(Continued)

*Primary Examiner* — J. Christopher Ball
(74) *Attorney, Agent, or Firm* — Danielson Legal LLC

(57) ABSTRACT

A system for obtaining a pH measurement includes a disposable probe and a reader. The disposable probe comprises multiple indicating electrodes and at least one reference electrode. The reader is configured to operably engage with the disposable probe and provide pH information of a sample.

17 Claims, 10 Drawing Sheets

(51) Int. Cl.
*B01L 3/00* (2006.01)
*G01N 27/403* (2006.01)
*G01N 33/483* (2006.01)

(52) U.S. Cl.
CPC ...... *G01N 27/307* (2013.01); *B01L 2200/027* (2013.01); *B01L 2200/0673* (2013.01); *B01L 2300/0645* (2013.01); *B01L 2300/087* (2013.01); *B01L 2300/0816* (2013.01); *B01L 2300/0829* (2013.01); *B01L 2300/1827* (2013.01); *B01L 2400/0406* (2013.01); *B01L 2400/049* (2013.01); *B01L 2400/0427* (2013.01); *B01L 2400/0677* (2013.01); *G01N 27/4035* (2013.01); *G01N 33/4836* (2013.01)

(58) Field of Classification Search
CPC ....... B01L 3/502738; B01L 2200/0673; B01L 2200/027; B01L 2300/087; B01L 2300/0816; B01L 2300/0829; B01L 2300/1827; B01L 2300/0645; B01L 2400/0427; B01L 2400/049; B01L 2400/0677; B01L 2400/0406

See application file for complete search history.

(56) References Cited

U.S. PATENT DOCUMENTS

| | | |
|---|---|---|
| 5,480,534 A | 1/1996 | Kato et al. |
| 6,652,720 B1 | 11/2003 | Mansouri et al. |
| 7,410,616 B2 | 8/2008 | Santini, Jr. et al. |
| 2005/0147741 A1 | 7/2005 | Hsiung et al. |
| 2006/0054504 A1 | 3/2006 | Lee et al. |
| 2007/0163884 A1 | 7/2007 | Strand et al. |
| 2008/0034972 A1 | 2/2008 | Gough et al. |
| 2008/0078680 A1 | 4/2008 | Marquant |
| 2010/0116646 A1 | 5/2010 | Hanzalova |

OTHER PUBLICATIONS

Translation of Official Action for JP2014-528702, undated, 6 pages.
Supplementary European Search Report for EP 12830258, dated Sep. 15, 2015, 7 pgs.
Patent Examination Report No. 1 for 2012304637, dated Jan. 7, 2015, 3 pgs.
Patent Examination Report No. 2 for 2012304637, dated Jan. 30, 2015, 3 pgs.
Patent Examination Report No. 3 for 2012304637, dated Mar. 5, 2015, 3 pgs.
Translation of DE102009007851, dated Feb. 26, 2016, 5 pgs.
International Search Report for PCT/US2012/053902, dated Dec. 7, 2012, 2 pages.
International Preliminary Report on Patentability for PCT/US2012/053902, dated Mar. 12, 2014, 7 pages.

* cited by examiner

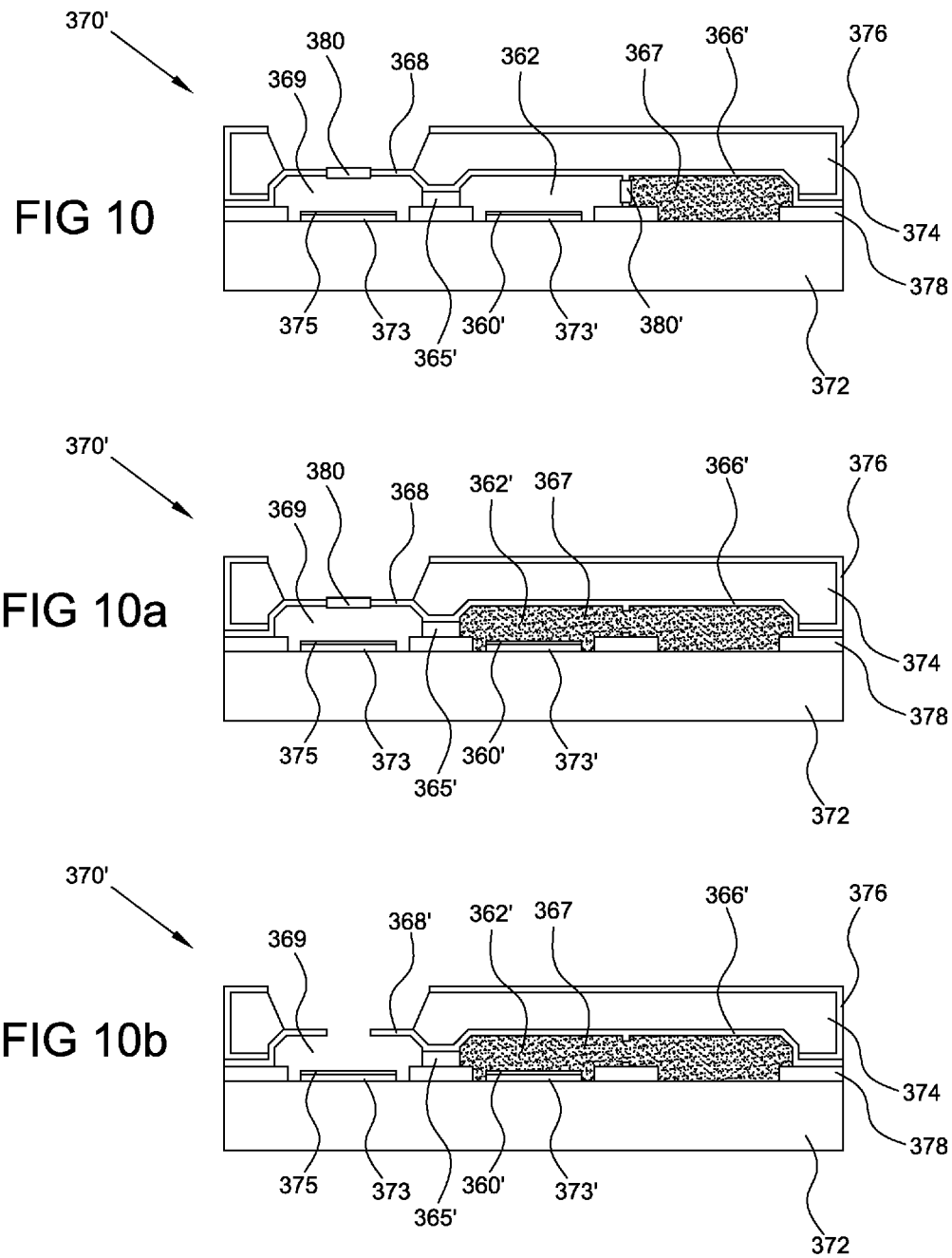

MEASUREMENT DEVICE WITH SENSOR ARRAY

CROSS-REFERENCE TO RELATED APPLICATIONS

This application is the national phase of International (PCT) Patent Application No. PCT/US2012/053902, filed on Sep. 6, 2012, published under PCT Article 21(2)in English, which claims priority to and benefit of U.S. Provisional Application No. 61/531,238, entitled MEASUREMENT DEVICE WITH SENSOR ARRAY, by Clark et al, filed on Sep. 6, 2011, the disclosures of each of which are incorporated herein by reference in their entirety.

BACKGROUND OF THE INVENTION

The following information is provided to assist the reader to understand the technology described below and certain environments in which such technology can be used. The terms used herein are not intended to be limited to any particular narrow interpretation unless clearly stated otherwise in this document. References set forth herein may facilitate understanding of the technology or the background thereof. The disclosures of all references cited herein are incorporated by reference in their entirety.

A typical pH sensor based on potentiometric principles includes a reference electrolyte solution, an indicating electrode immersed in or in contact with an analyte solution (of which the pH is to be measured), a reference electrode immersed in the reference electrolyte solution, and measurement circuitry such as potentiometric circuitry in electrical connection with the reference electrode and the indicating electrode. The potentiometric circuitry measures the electrical difference between the indicating and reference electrodes. Ionic contact between the electrolyte solutions in which the indicating electrode and the reference electrodes are immersed provides electrical connection between the electrodes. The pH value of the sample or analyte electrolyte solution (which is proportional to concentration of the hydrogen ions in the sample electrolyte) is directly correlated with the potential difference developed at the indicating electrode following the Nernst equation.

In the above-described configuration, an important condition for correct measurement is that the electric potential difference built up in the reference electrode and the reference electrolyte is maintained constant such that the reading from the potentiometric circuitry solely represents the potential difference in the indicating electrode, that is, pH in the electrolyte solution. To meet this condition, a common arrangement is to have the reference electrode immersed in a saturated reference electrolyte solution, and to have a small "window" positioned between the saturated reference electrolyte solution and the sample or analyte electrolyte solution to provide ionic contact and thus an electrical connection between the saturated reference electrolyte solution and the sample or analyte electrolyte solution. The "window" is usually fabricated from a porous material such as a porous glass membrane, a hydrophilic porous polymer membrane, etc. Because of the porosity of the "window", a non-negligible mass exchange occurs between the saturated reference electrolyte solution and the sample or analyte electrolyte solution, thereby causing cross-contamination in both solutions.

The dilution of the saturated reference electrolyte solution resulting from such contamination can be a significant problem since it changes the potential difference in the reference electrode. The contamination also deteriorates the stability of the pH sensor and shortens the lifetime of the pH sensor. As the dimensions of a pH sensor are reduced (for example, to very small, microlevel, microscale or smaller dimension), the problem is exacerbated because the volume of the saturated reference electrolyte solution is very small compared to the sample electrolyte solution. For example, for applications where a microscale or smaller pH sensor is implanted into a human body and is utilized to measure a physiological pH (for example, myocardial pH), the volume of the saturated reference electrolyte solution is extremely small compared to the volume of the myocardial tissue of which the pH is to be measured. At such a scale, the saturated reference electrolyte solution is diluted much more quickly than in a macro scale glass tube type pH sensor.

Another factor which affects the useful life of a pH sensor, such as a microscale pH sensor, is the durability of the reference electrode. In many instances, conductive material of the reference electrode is gradually dissolved and consumed into the saturated reference electrolyte solution. At some point during the dissolution and consumption of the reference electrode, the useful life of the pH sensor is terminated.

SUMMARY

According to a first aspect of the inventive concepts, a system for obtaining a pH measurement is disclosed. The system comprises a disposable probe and a reader. The disposable probe includes multiple indicating electrodes and at least one reference electrode. The reader is constructed and arranged to operably engage with the disposable probe and provide pH information to a sample.

In some embodiments, the disposable probe includes multiple controllable orifices, such as a first controllable orifice constructed and arranged to provide a first fluid pathway to a first indicating electrode, and a second controllable orifice constructed and arranged to provide a second fluid pathway to a second indicating electrode. In an alternative embodiment, a first controllable orifice is constructed and arranged to provide a fluid pathway to a first indicating electrode, and a second controllable orifice is constructed and arranged to create a second fluid pathway to a first reference electrode.

The system may include an electronics module configured to activate one or more controllable orifices, such as an electronics module positioned in the reader. The reader may comprise a user interface configured to communicate with the electronics module, such as to display pH information and allow information to be input by an operator of the system. The electronic module may include memory and other electronic microcontroller components. These components may be used to serially index from one controllable orifice to another (e.g. through the use of a lookup table stored in memory), such as to selectively open fluid pathways to a first electrode, then a second electrode, and so on. The fluid pathways may be fluidly connected to one or more solutions, such as reference solutions and/or sample solutions, such that these fluids can be operably delivered to an electrode such as an indicating electrode and/or a reference electrode.

In some embodiments, the controllable orifice comprises a membrane, such as a multi-layer membrane. A heating element may be positioned within, on or proximate to the membrane such as to cause the membrane to rupture or otherwise open when the heating element is activated (e.g. due to mechanical forces created by a change in temperature). The heating element may comprise a coil configured to heat as current is passed therethrough, such as a coil made of gold and/or chromium or other metal. The membranes and/or heating elements of the current inventive concepts may be made by a MEMS or other automated and/or layered manufacturing process.

The indicating electrodes of the present inventive concepts may comprise iridium oxide electrodes. The disposable probe may include multiple indicating electrodes such as at least 9, at least 30 or at least 90 indicating electrodes. In one embodiment, the disposable probe comprises three or more indicating electrodes and at least two reference electrodes. The reference electrodes may comprise silver-silver chloride electrodes and/or iridium oxide electrodes.

The indicating and/or reference electrodes of the present inventive concepts may be surrounded by a walled chamber. The chamber may comprises a vacuum chamber (e.g. a chamber with an environment in a full or partial vacuum), such as to draw a solution such as a sample solution into the chamber. Alternatively, one or more vents may be in fluid communication with the chamber such as to improve administration of fluid such as sample fluid into the chamber. The chamber may comprise a hydrophilic material and/or include a coating such as a hydrophilic coating. Alternatively or additionally, the walls of the chamber may otherwise be constructed and arranged (e.g. sloped) to draw solution or otherwise improve flow of solution into the chamber.

The indicating and/or reference electrodes of the present inventive concepts may be mounted to a substrate, with or without a mounting pad such as a titanium mounting pad. The indicating and/or reference electrodes of the current inventive concepts may be made by a MEMS or other automated and/or layered manufacturing process.

The disposable probes of the present inventive concepts may include a liquid junction, and a cap may be included to prevent drying of the liquid junction and/or to otherwise protect the distal end of the disposable probe. Reference solution may be included in the system, such as potassium chloride (KCL) reference solution. One or more components of the system, such as the indicating or reference electrodes, may be mounted to a substrate such as a glass, silicon or plastic substrate. Numerous combinations of two or more indicating electrodes and one or more reference electrodes may be mounted to the substrate.

The system of the present inventive concepts may include one or more sensors, such as one or more sensors used by an electronics module of the system to determine a pH reading and/or to aid in calibration of a pH reading. Typical sensors include but are not limited to: a pressure sensor; a humidity sensor; and combinations of these. In one embodiment, the sensor is included in the reader. Alternatively or additionally, a sensor may be included in the disposable probe.

In a typical embodiment, the system of the present invention includes multiple disposable probes, each constructed and arranged to operably engage a reader.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

FIG. 10 illustrates a cross sectional view of another embodiment of an array of sensors.

FIG. 10a illustrates a cross sectional view of the array of FIG. 10 after a first orifice has been opened.

FIG. 10b illustrates a cross sectional view of the array of FIG. 10 after a second orifice has been opened.

DETAILED DESCRIPTION OF THE DRAWINGS

Figure 1:
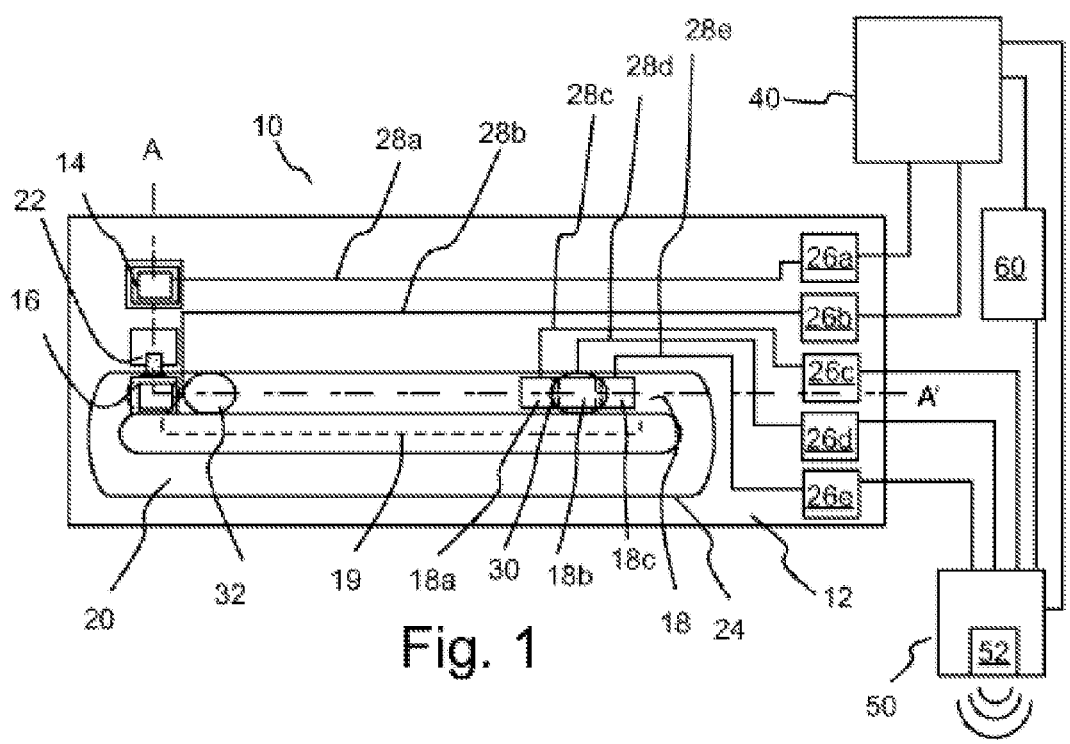
FIG. 1 illustrates a top view of an embodiment of a pH sensor.

Reference will now be made in detail to the present embodiments of the technology, examples of which are illustrated in the accompanying drawings. The same reference numbers are used throughout the drawings to refer to the same or like parts.

As used herein and in the appended claims, the singular forms "a," "an", and "the" include plural references unless the content clearly dictates otherwise. Thus, for example, reference to "a bubble" includes a plurality of such bubbles and equivalents thereof known to those skilled in the art, and so forth, and reference to "the bubble" is a reference to one or more such bubbles and equivalents thereof known to those skilled in the art, and so forth.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "attached", "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

FIG. 1 illustrates a top view of a pH sensor 10 according to various embodiments which is readily formed to microscale or smaller (for example, nanoscale) dimensions, such as a pH sensor described in International Application Serial Number PCT/US2010/045847, the contents of which are incorporated herein by reference in its entirety. The term "microscale" as used in connection with the pH sensor hereof refers to sensors having dimensions smaller than one centimeter. In a number of embodiments, the dimensions of the pH sensors hereof are amenable to micro- and/or nanofabrication techniques. In a number of embodiments, the reference electrolyte solution volume was 20 cubic mm or less.

Figure 2:
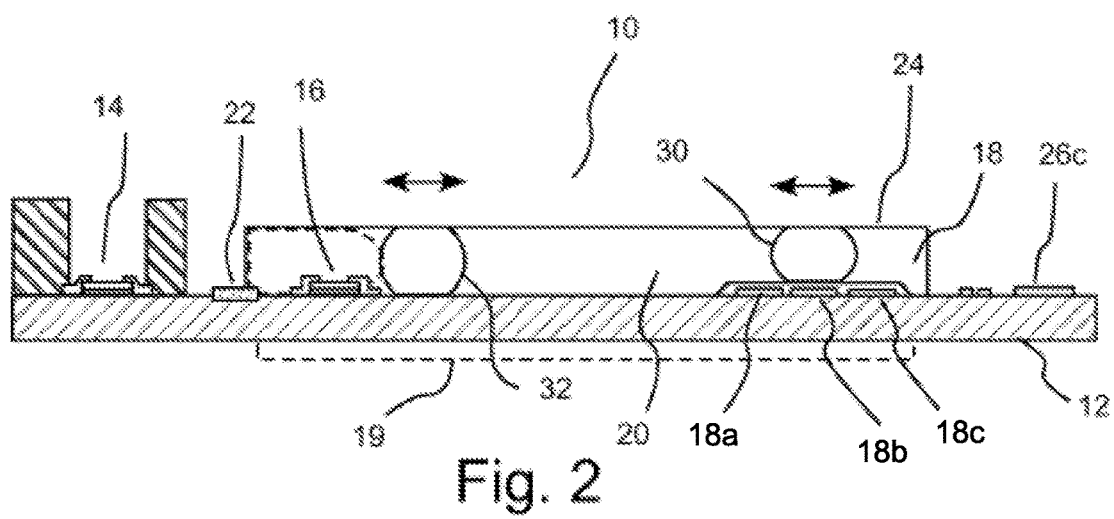
FIG. 2 illustrates a cross-sectional view of the pH sensor of FIG. 1 along A-A' illustrated in FIG. 1.

FIG. 2 illustrates a cross-sectional view of pH sensor 10 (taken along line A-A' illustrated in FIG. 1). In a number of embodiments, pH sensor 10 can, for example, be formed in a size and configuration which allows for its implantation into a body (that is, within a human or animal) using a minimally invasive technique. In a number of embodiments, the length, width and height of pH sensor were each less than 1 centimeter. Such a microscale pH sensor 10 may, for example, be used in a variety of applications to measure the pH of a sample electrolyte, a sample tissue, etc. Such applications include medical applications where the microscale pH sensor 10 is utilized to measure the pH of myocardial tissue, brain tissue, liver tissue, kidney tissue, lung tissue, etc.

In the representative embodiment of FIGS. 1 and 2, pH sensor 10 includes a substrate 12, a first electrode 14, a second electrode 16, a system for transporting a bubble 18, a fluidic closed loop channel 20, a liquid junction 22, a cover 24, a plurality of connection pads 26a through 26e, and a plurality of conductors 28a through 28e (see FIG. 1).

Substrate 12 may, for example, include any suitable type of material that is, for example, amenable to fabrication of the various electrodes and other layers that it supports. Suitable materials include, for example, silicon-based materials (for example, silicon, glass etc.), non-silicon-based materials, polymeric materials (for example, polydimethylsiloxane or PDMS) and other materials. In the case the sensor is to be implantable within a body, the material can, for example, be bio-compatible. In a number of embodiments, for example, substrate 12 is a glass substrate. The first electrode 14 functions as an indicating or sensing electrode, and may, for example, include any suitable type of material. In general, it is desirable that the material for first electrode 14 exhibit a wide pH response range, high sensitivity, fast response time, low potential drift, in sensitivity to stirring, a wide temperature operating range and a wide operating pressure range.

First electrode 14 can, for example, include an ion-selective field effect transistor (ISFET) or a metal oxide electrode. An ISFET is part of a solid-state integrated circuit. The ISFET exhibits a fast response time (on the order of 1 millisecond) and is quite rugged in in-vivo applications.

In the case of a metal oxide electrode, a number of metal oxides are suitable for use in first electrode 14. Metal oxides can, for example, be deposited upon a conductive (for example, metallic) layer that is deposited or formed on substrate 12. A metal oxide film or layer (for example, iridium oxide) can, for example, be created via a variety of techniques including electrochemical oxidation via potential cycling, reactive sputtering, anodic electrodeposition, thermal oxidation and others. In a number of embodiments, first electrode 14 includes platinum and iridium oxide. For such embodiments, the platinum can be deposited on the substrate 12, and the iridium oxide can be formed or deposited on the platinum. According to other embodiments, the first electrode 14 includes chromium and iridium oxide. For such embodiments, the chromium can be formed on the substrate 12, and the iridium oxide can be formed on the chromium. According to other embodiments, the first electrode 14 includes titanium and iridium oxide. For such embodiments, the titanium can be formed on the substrate 12, and the iridium oxide can be formed on the titanium. The first electrode 14 is positioned so that it comes into contact with the sample solution/electrolyte (for example, within a sample tissue) of which the pH is to be measured.

Second electrode 16 functions as a reference electrode, and may include any suitable type of material. Desirably, reference electrode 16 maintains a constant or substantially constant potential in the electrolyte solution. In a number of embodiments, second electrode 16 includes platinum and silver. For such embodiments, the platinum can, for example, be formed or deposited on substrate 12, and the silver can be formed or deposited on the platinum. According to other embodiments, second electrode 16 includes platinum and silver chloride. For such embodiments, the platinum can, for example, be formed or deposited on substrate 12, and the silver chloride can be formed or deposited on the platinum. According to other embodiments, second electrode 16 includes chromium and silver. For such embodiments, the chromium can, for example, be formed or deposited on the substrate 12, and the silver can formed on the chromium. According to other embodiments, second electrode 16 includes chromium and silver chloride. For such embodiments, the chromium can, for example, be formed or deposited on substrate 12, and the silver chloride can be formed on the chromium. According to other embodiments, second electrode 16 includes titanium and silver. For such embodiments, the titanium can, for example, be formed or deposited on substrate 12, and the silver can be formed on the titanium. According to other embodiments, second electrode 16 includes titanium and silver chloride. For such embodiments, the titanium can, for example, be formed or deposited on the substrate 12, and the silver chloride can be formed or deposited on the titanium. Second electrode 16 is positioned so that it is in contact with a reference solution within fluidic closed loop channel 20.

Bubble transport system 18 and bubbles 30 and 32 operate in connection with liquid junction 22 and the reference analyte solution within fluidic channel 20 as a fluidic switch or controller 19. Fluidic switch 19 is, for example, operable to place pH sensor 10 in an on state or in an off state. Fluidic switch 19 may be any type of fluidic switch suitable to provide a barrier between a fluid transporting member such as liquid junction 22 and the reference electrolyte solution. In a number of embodiments, fluidic switch 19 is operable to turn pH sensor 10 (or another device) off and on by, for example, disrupting the ionic electrical connection between the analyte solution and the reference solution. Fluidic switch 19 can also be operable to reduce or eliminate mass transfer between the analyte solution and the reference solution.

In a number of embodiments, as described in more detail hereinafter, bubble transport system 18 can, for example, use electrowetting-on-dielectric principles to effect switching functionality. According to various embodiments, bubble transport system 18 can, for example, include a plurality of electrodes. In the illustrated embodiment, bubble transport system 18 includes three electrodes 18a, 18b and 18c. Bubble transport system 18 may include any suitable type of material. In various embodiments, bubble transport system 18 includes platinum, an insulating layer (e.g., silicon oxide, parylene, etc.), and a hydrophobic layer (e.g., a fluorocarbon hydrophobic layer). In such embodiments, the platinum can, for example, be formed or deposited on substrate 12, and the insulating layer and the hydrophobic layer can be formed or deposited on the platinum. According to other embodiments, bubble transport system 18 includes chromium, an insulating layer, and a hydrophobic layer. For such embodiments, the chromium can, for example, be formed or deposited on substrate 12, and the insulating layer and the hydrophobic layer can be formed or deposited on the chromium. Bubble transport system 18 is positioned so that it is in direct contact with the reference solution of fluidic closed loop channel 20.

In the representative embodiment of FIGS. 1 and 2, fluidic channel 20 is a closed loop channel 20 which is collectively defined by substrate 12 and cover 24. Fluid closed loop channel 20 can, for example, include any suitable type of ionically conductive aqueous solution. For example, according to various embodiments, fluidic channel 20 includes a saturated potassium chloride solution. According to other embodiments fluidic channel 20 includes a saturated silver chloride solution. Fluidic channels hereof need not be closed loop fluid channels. The fluidic channels enable movement of one or more bubbles or, in the case where a bubble is generated within the channel as described below, the fluidic channel allows displacement of the liquid so that the one or more bubbles can be formed to a desired volume.

As shown in FIG. 1, in a number of embodiments, fluidic closed loop channel 20 surrounds bubble transport system 18, and includes a first bubble 30 and a second bubble 32. First bubble 30 is hydrodynamically connected to the second bubble 32 via the saturated reference solution. Thus, when first bubble 30 is driven from a first position to a second position, second bubble 32 moves from a third position to a fourth position. The third position is shown in solid lines in FIGS. 1 and 2, while the fourth position is show in dashed lines in FIGS. 1 and 2. Accordingly, first bubble 30 may be considered a "master" bubble and second bubble 32 may be considered a "slave" bubble. First and second bubbles 30 and 32 may, for example, include any suitable type of fluid material immiscible in the reference solution. At least bubble 32 can, for example, be immiscible in the analyte solution. For example, according to various embodiments, first and second bubbles 30 and 32 may include air, oil, a gas other than air (for example, hydrogen, oxygen, a mixture of oxygen and hydrogen, etc), etc.

As used herein, the term "bubble" refers to a globule or volume of one substance (a fluid) in another fluid (the reference electrolyte solution). A bubble can, for example, be formed of a gas that is immiscible in the liquid within channel 20 (that is, the saturated reference solution) or a liquid that is immiscible in the liquid within channel 20.

Liquid junction 22 is positioned between the sample or analyte electrolyte solution and the reference solution enclosed in fluidic closed loop channel 20 (for example, saturated potassium chloride), and provides for ionic electrical connection between the analyte electrolyte solution and the reference solution in fluidic closed loop channel 20. In a number of embodiments, liquid junction 22 is a member through which fluid transport can occur and may, for example, include a porous or permeable material. For example, according to various embodiments, liquid junction 22 includes a hydrophilic porous polymer. A porous material for liquid junction 22 can, for example, have a pore size of less than one micrometer. In a number of embodiments, liquid junction 22 is designed to limit or minimize mass exchange between the solution in the fluidic closed loop channel 20 and the sample electrolyte solution (for example, by limiting pore size in the case of a porous material). As shown in FIG. 2, liquid junction 22 is positioned between the substrate 12 and the cover 24 in the illustrated embodiment.

Cover 24 is connected to substrate 12, and cooperates with substrate 12 to define fluidic closed loop channel 20. Cover 24 may, for example, include any suitable type of impermeable material. In the case of an implantable pH sensor 10, cover 24 (and other components of pH sensor 10 which contact an organism) can, for example, be biocompatible. For example, according to various embodiments, cover 24 includes glass or polydimethylsiloxane. Cover 24 may be connected to the substrate 12 in any suitable manner. For example, according to various embodiments, the cover 24 is bonded to the substrate 12. In several embodiments in which cover 24 is glass and substrate 12 is PDMS, cover 24 is readily bonded to substrate 12 by simply pressing them together after $O_2$ plasma treatment of surfaces. In, for example, cases in which the fluidic channel 20 width is relatively large (for example, about 1 mm or larger) an adhesive can be used to bond cover 24 to substrate 12.

As described above, in the illustrated representative embodiment of FIGS. 1 and 2, a plurality of connection elements or pads 26a through 26e are connected to substrate 12, and may include any suitable type of conductor. For example, according to various embodiments, connection pads 26a-e include platinum. According to other embodiments, connection pads 26a-e include chromium. According to other embodiments, connection pads 26a-e include titanium. According to other embodiments, connection pads 26a-e include gold. Connection pad 26a is connected to the first electrode 14 via conductor 28a. Connection pad 26b is connected to second electrode 16 via conductor 28b. Connection pads 26c, 26d and 26e are connected to electrodes 18a, 18b and 18c of bubble transport system 18 via the conductors 28c, 28d and 28e, respectively. Connection pads 26a-e provide for electrical connection of first electrode 14, second electrode 16, and electrodes 18a, 18b and 18c of fluidic switch 18 to one or more circuits external to the pH sensor 10. As illustrated in FIG. 1, first electrode 14 and second electrode 16 can, for example, be connected to measurement electronics or circuitry 40 which can, for example, include potentiometer circuitry as known in the art. Electrodes 18*a*, 18*b* and 18*c* of bubble transport system 18 can, for example, be in electrical connection with control electronics or circuitry 50.

The plurality of conductors 28*a-e* may, for example, be formed on a surface of substrate 12, and function to connect first electrode 14, second electrode 16, and electrodes 18*a-c* to respective connection pads 26*a-e*. As shown in FIG. 1 and as described above, a first conductor 28*a* connects first electrode 14 to first connection pad 26*a*, and a second conductor 28*b* connects second electrode 16 to second connection pad 26*b*. Similarly, individual conductors 28*c-e* connect electrodes 18*a-c* of bubble transport system 18 to corresponding connection pads 26*c-e*, respectively. Conductors 28*a-e* may, for example, include any suitable type of conductive material. For example, according to various embodiments, conductors 28*a-e* include platinum. According to other embodiments, conductors 28*a-e* include chromium. According to other embodiments, conductors 28*a-e* include titanium. According to other embodiments, conductors 28*a-e* include gold.

In operation of the representative embodiment illustrated in FIGS. 1 and 2, first electrode 14 is exposed to the sample electrolyte (or to a sample tissue). When pH sensor 10 is in an off state (via fluidic switch 19), first bubble 30 is positioned on the "leftmost" (in the orientation the figures) electrode 18*a* of bubble transport system 18, and second bubble 32 is positioned against liquid junction 22. The positioning of the first bubble 30 and second bubbles 32 may, for example, be realized in any suitable manner. For example, according to various embodiments, electrowetting-on-dielectric techniques may be utilized to move the first bubble 30 and second bubble 32 to the respective positions. For such embodiments, the sequential activation of "rightmost" electrode 18*c* and "middle" electrode 18*b* of bubble transport system 18 may be utilized to cause first bubble 30 and second bubble 32 to move to the respective positions associated with the off state of pH sensor 10.

In the off state position, second bubble 32 can, for example, form a barrier over second electrode 16 and liquid junction 22, effectively blocking the fluid/electrical (ionic) connection between the sample electrolyte and the saturated solution in the fluidic closed loop channel 20, thereby reducing or preventing the dissolution of second electrode 16 into the saturated solution, and reducing or preventing mass exchange through liquid junction 22. When second bubble 32 is in the above-described, off-state position, immiscible phase interfaces (for example, gas-liquid or liquid-liquid immiscible interfaces) are formed between second bubble 32 and the sample electrolyte in or at the surface of the pores of liquid junction 22. The interfacial tension between the phases, for example, between a gas and the liquid phase) operates to reduce or block leakage of the sample electrolyte into fluidic closed loop channel 20. Maintaining pH sensor 10 in an off state extends the useful life of pH sensor 10 as compared to a sensor continuously maintained in an on state.

When a pH level is to be measured, pH sensor 10 is switched to an on state. To be switched to the on state, second bubble 32 is moved so that it does not form a barrier over second electrode 16 and the liquid junction 22, and thereby allows for the establishment of an electrical connection between the sample electrolyte and the saturated solution in fluidic closed loop channel 20. According to various embodiments, second bubble 32, which is hydrodynamically connected to first bubble 30, is moved away from second electrode 16 and liquid junction 22 by moving first bubble 30 away from "leftmost" electrode 18*a* of bubble transport system 18.

First bubble 30 may be moved away from "leftmost" electrode 18*a* of bubble transport system 18 in any suitable manner. For example, according to various embodiments, electrowetting-on-dielectric principles are utilized to move first bubble 30, which in turn causes movement of second bubble 32. In electrowetting-on-dielectric devices or systems, bubbles are transported by programming and sequentially activating arrays of electrodes.

For such embodiments, the activation of "leftmost" electrode 18*a* of bubble transport system 18 operates to move first bubble 30 away from "leftmost" electrode 18*a* of bubble transport system 18 and towards "rightmost" electrode 18*c* of bubble transport system 18. The movement of first bubble 30 towards the "rightmost" electrode 18*c* of bubble transport system 18 causes second bubble 32 to move away from second electrode 16 and liquid junction 22, thereby removing the barrier over second electrode 16 and liquid junction 22. The removal of the barrier allows for the establishment of the fluid/electrical (ionic) connection between the sample electrolyte and the saturated solution in fluidic closed loop channel 20.

In the manner described above, pH sensor 10 can be quickly switched between the off and on states, with very low energy consumption. By forming a barrier over second electrode 16 and liquid junction 22 during the off state, and exposing second electrode 16 and liquid barrier 22 to the saturated reference solution of the fluidic closed loop channel 20 only during the on state, dissolution of the second electrode 16 and mass exchange through the liquid junction 22 is reduced or minimized, thereby increasing the useful life of pH sensor 10.

As illustrated schematically in FIG. 1, at least one power source 60 such as a battery can be provided in electrical connection with sensor electronics 40 and control electronics 50. Power source 60 can, for example be used to power sensor electronics 40, control electronics 50 and bubble transport system 18 in the embodiment of FIG. 1. In a number of embodiments, pH sensor 10 can, for example, be actuatable and/or controllable via an external device 70 which communicates (for example, wirelessly via, for example, a radio frequency or RF signal) with, for example, a transceiver 52 in communicative connection with control electronics 50. Control electronics 50 can, for example, be programmed (for example, via one or more programmed processors) to cause bubbles 30 and 32 to move as describe above to enable pH sensor 10 to measure pH at some predetermined time cycle and/or in response to an external signal (for example, external to a body in which pH sensor 10 is implanted). When pH sensor 10 is activated or enabled, a pH reading is acquired by sensor electronics 40. Sensor electronics 40 is in communicative connection with control electronics 50 which effects control of bubble transport system 18. Once a measurement is obtained, pH sensor 10 can be placed in the off state or inactivated via control of bubble transport system 18 as described above. The measured pH value can, for example, be made available for use (for example, either for transmission to outside the body via transceiver 52, or for use by another implanted system, which can, for example, include a treatment device).

Figure 3:
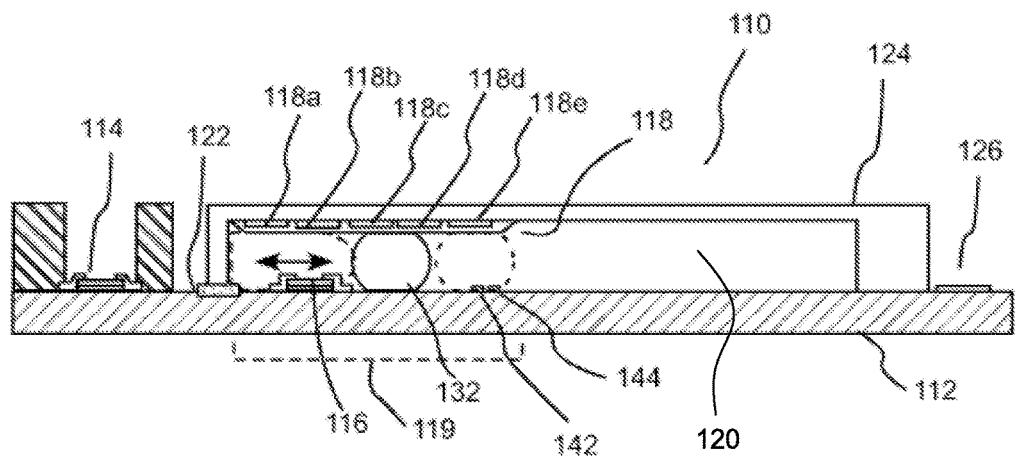
FIG. 3 illustrates a cross-sectional view of another embodiment of a pH sensor.

In several embodiments of the present invention, a pH sensor includes a single bubble to effect switching between an on state and an off state. For example FIG. 3 illustrates another representative embodiment of a pH sensor 110 in which a single bubble 132 within a channel 120 (formed between a cover 124 and a substrate 112) is used to form a barrier over a second or reference electrode 116 and a liquid junction 122 (as described in connection with pH sensor 10) to operate as a fluidic switch or controller 119. As described above, by forming or creating a barrier covering liquid junction 22, an off-state is created, wherein ionic electrical connection between the analyte solution (which contacts first or indicating electrode 114) and the reference solution within channel 120 is disrupted or prevented. Furthermore, in the off-state, bubble 132 reduces, minimizes or eliminates mass transfer between the analyte solution and the reference solution. The off state further reduces dissolution of electrode 116 within the reference solution. If bubble 132 is of sufficient size to cover electrode 116, dissolution (mass transfer) between electrode 116 and the reference solution can be further reduced, minimized or eliminated. Dissolution of second electrode 116 and mass exchange through the liquid junction 122 thus occurs to a significant extent only during the on state, thereby increasing the useful life of pH sensor 110.

In the embodiment of FIG. 3, gas bubble 132, which is a mixture of oxygen and hydrogen, is generated via electrolysis using an anode 142 and a cathode 144 that are positioned relatively close to each other (for example, within approximately 4 um in several embodiments). In the embodiment illustrated in FIG. 3, bubble transport system 118 (for example, an electrowetting-on-dielectric system) is positioned on a top surface of fluidic channel 120. Bubble transport system 118, can, for example, include an array of electrodes 118a-e, which are positioned on an inner surface of cover 124 (that is, on a top surface of fluidic channel 120). In the illustrated embodiment, the electrolysis electrodes used to create bubble 132 (that is, anode 142 and cathode 144) are placed on substrate 112. To create bubble 132 (or a plurality of bubbles as, for example, discussed in connection with pH sensor 10 of FIGS. 1 and 2), one can, for example, apply a potential difference of approximately 5 V between and anode/cathode pair such as anode 142 and cathode 144.

In operation of fluidic switch 119, bubble 132 is first generated via electrolysis using anode 142 and cathode 144 (see rightmost dashed lines in fluidic channel 120). The size of the bubble created can, for example, be controlled via control of the time that a potential is applied. To place fluid switch 119 in an off state, bubble 132 is transported via bubble transportation system 118 to cover liquid junction 122 (see leftmost dashed lines in fluidic channel 120) and, in several embodiments, to cover reference electrode 116. To place fluid switch in an on state, bubble 132 is transported via bubble transportation system 118 so that is does not cover either liquid junction 122 or reference electrode 116.

Figure 4:
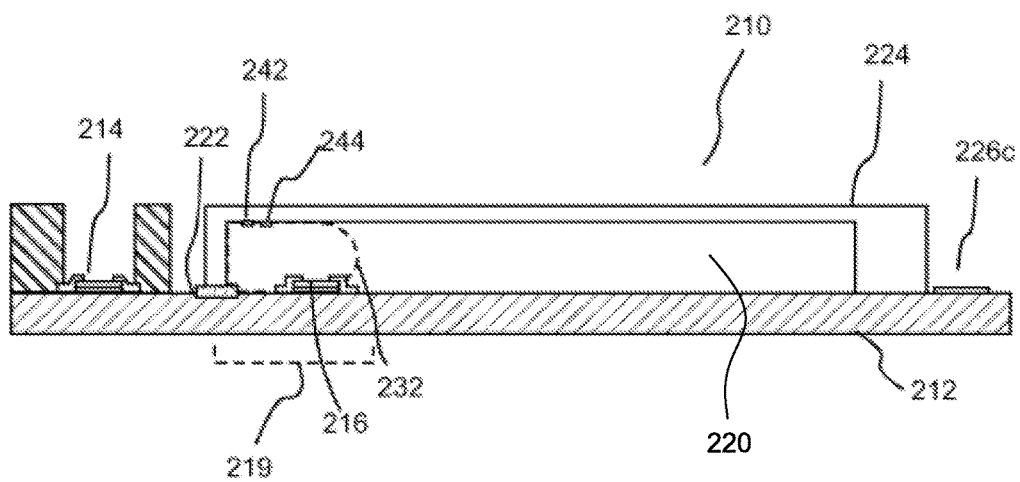
FIG. 4 illustrates a cross-sectional view of another embodiment of a pH sensor.

FIG. 4 illustrates another representative embodiment of a pH sensor 210 in which a single bubble 232 within a channel 220 (formed between a cover 224 and a substrate 212) is used to form a barrier over a second or reference electrode 216 and a liquid junction 222, as described in connection with pH sensors 10 of FIGS. 1 and 2 and pH sensor 110 of FIG. 3, to operate as a fluidic switch 219. As described above, by forming or creating a barrier covering liquid junction 222, an off-state is created, wherein ionic electrical connection between the analyte solution (which contacts first or indicating electrode 214) and the reference solution within channel 220 is disrupted or prevented. If bubble 232 is of sufficient size to cover electrode 216, dissolution (mass transfer) between electrode 216 and the reference solution can be further reduced, minimized or eliminated.

In operation of fluidic switch 219, bubble 232 is first generated via electrolysis using anode 242 and cathode 244 (see rightmost dashed lines in fluidic channel 220). As described above, the size of the bubble created can, for example, be controlled via control of the time that a potential is applied. To place fluid switch 219 in an off state, bubble 232 is generated to a size to cover liquid junction 222 and, in several embodiments, to cover reference electrode 216. To subsequently place fluid switch in an on state, bubble 232 is reduced in size or completely eliminated via reversing of the electrolysis process using anode 242 and cathode 244 so that it does not cover either liquid junction 222 or reference electrode 216. To effect bubble reduction or elimination, catalysis can be used to lower the energy barrier in the reverse process. For the case of bubble 232 including hydrogen and oxygen bubble, platinum (Pt) can, for example, be used as a catalyst. In a number of embodiments, anode 242 and cathode 244 can, for example, be made to include a catalytic material such as Pt. When an electric potential is applied to the anode 242 and cathode 244, bubble 232 grows. When the electric potential is shut off, bubble 232 shrinks. In an alternative embodiment, a source of a catalyst such as Pt can be provided separately from anode 242 and cathode 244.

Fluidic switches or controller such as fluidic switches or controllers 19 of FIGS. 1 and 2, 119 of FIG. 3, and 219 can, for example, be used in other devices where it is desirable to control fluid connection, ionic conduction and/or mass transfer across a member though which a fluid can be transported (for example, a porous or permeable member such as a porous polymeric member, a permeable membrane etc).

Figure 5:
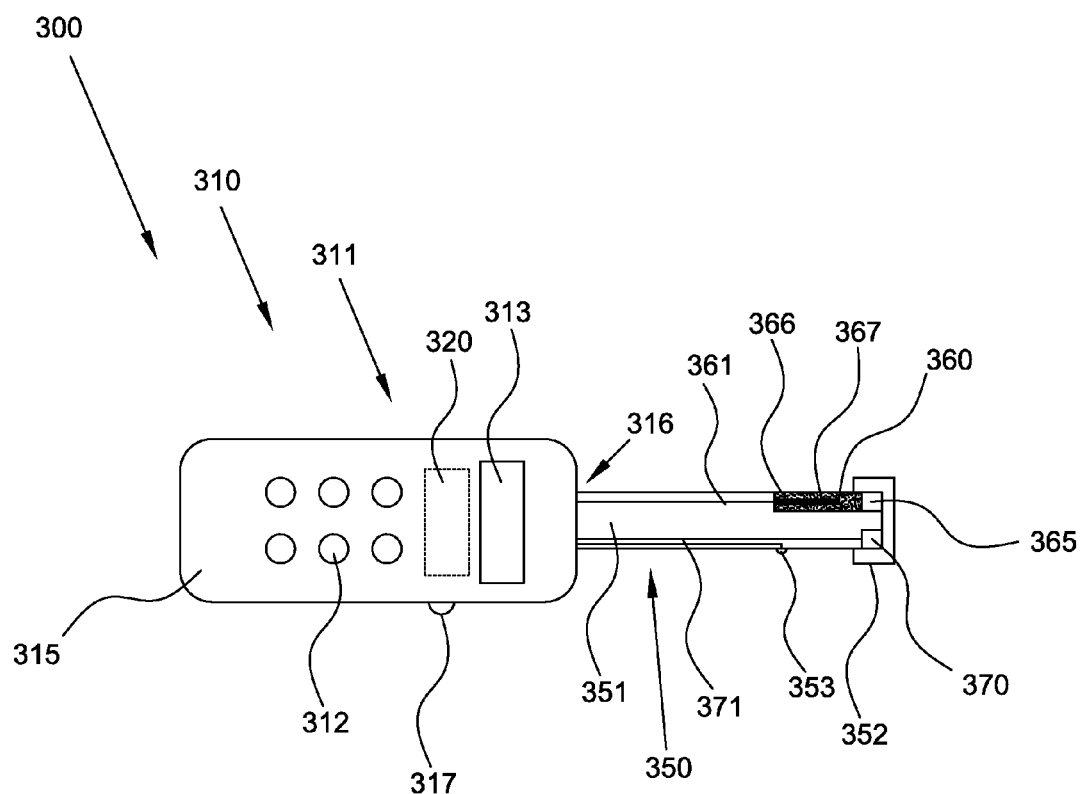
FIG. 5 illustrates a top view of an embodiment of a system comprising a disposable probe and a reader.

FIG. 5 illustrates an embodiment of a system for taking pH readings using a handheld device and multiple use sensing probes, according to embodiments of the present invention. System 300 comprises reader 310, and a disposable probe 350. In a typical configuration, operation of system 300 is based on potentiometric measurement of pH using an indicating electrode (e.g. an iridium oxide electrode) that is compared to a known electric potential generated by a reference electrode (e.g. a silver-silver chloride electrode) in contact with a reference solution. One or more components of system 300 are typically pre-conditioned to produce a known output, such as to avoid a calibration step, in manufacturing and/or at time of use. Reader 310 comprises housing 315 into which is integrated user interface 311. User interface 311 includes display 313 and buttons 312. Display 313, typically a liquid crystal or touch screen display, may display measured pH readings, as well as system and other information. System information may include but is not limited to: system readiness information; power levels; alert or alarm condition information; current status of disposable; and combinations of these. Other information provided by system 300 via user interface 311 may include environmental conditions such as temperature, humidity and/or pressure information recorded by sensor 317 of reader 310 or sensor 353 of probe 350.

Housing 315 further includes an electromechanical port, port 316, configured to operably engage with the proximal end of disposable probe 350. Probe 350 comprises housing 351, indicating electrode assembly 370, and liquid junction 365. Liquid junction 365 is typically constructed and arranged as is described above in reference to FIGS. 1 through 4. Indicating electrode assembly 370 comprises multiple indicating electrodes, each of which is independently activatable. In a typical embodiment, electrode assembly 370 is manufactured in a MEMS fabrication process, such as an iridium oxide electrode assembly manufactured in a MEMS process. In one embodiment, electrode assembly 370 comprises nine indicating electrodes, such as are described in reference to FIG. 6 herebelow. Numerous configurations of electrodes may be included such as arrays of ninety or more indicating and/or reference electrodes. Probe 350 also comprises reservoir 366, which houses reference solution 367 and reference electrode 360. Reference electrode 360 may be a silver/silver-chloride reference electrode, or another known reference source configured with predictable pH sensitivity when in contact with a known reference solution. In one embodiment, reference electrode 360 is an iridium oxide electrode. Alternative materials and combinations of materials can be used for reference electrode 360, such as those described in reference to FIGS. 1 through 4 hereabove. Reference solution 367 may be a KCl solution, or other suitable solution to be used in cooperation with reference electrode 360. Wires 361 and wire bundle 371 travel through housing 351 to port 316 such as to electrically connect reference electrode 360 and indicating electrode assembly 370, respectively, to electronics module 320. Module 320, contained within housing 315 of reader 310, is configured to determine pH levels based on electrical signals received on wires 361 and wire bundle 371 and to display pH information on display 313. Module 320 is typically configured to automatically index from a first indicating electrode to a second indicating electrode, such as to take a first measurement followed by a second measurement. Module 320 may be configured to index through numerous electrodes, such as through the use of a lookup register indicating the last electrode activated. Indicating electrodes may be activated or otherwise selected, such as by opening of a membrane or other controllable orifice, as is described in detail herebelow. Module 320 may be further configured to interpret other information such as signals received from sensor 353 and/or sensor 317. Module 320 may be further configured to store data, communicate with one or more external devices (e.g. via wired or wireless communications), perform internal diagnostic checks, and the like. Stored data may include but is not limited to: reference electrode 360 information; indicating electrode assembly 370 information; storage information; date of manufacture and other date information; and combinations of these. Liquid junction 365, when saturated with reference solution 367, allows electrical connection between indicating electrode assembly 370 and reference electrode 360 when probe 350 is submersed in a sample solution. Probe 350 may include a removable cap, cap 352, typically a plastic material that attaches to the distal tip of probe 350 and which is removed prior to testing of a sample solution. Cap 352 may be configured to prevent liquid junction 365 from drying out (e.g. during storage or between uses) or otherwise to protect the distal portion of probe 350.

Indicating electrode assembly 370 comprises multiple indicating electrodes configured to be independently activatable, such as to perform multiple measurements with a single probe 350. These multiple measurements may be made in succession, such as over a time period of minutes to hours, and/or over a longer time period such as weeks to months. User interface 311 is configured to allow an operator to individually activate each indicating electrode of electrode assembly 370, such as by electronics module 320 issuing one or more activation signals to assembly 370. Numerous configurations of activatable indicating electrodes may be employed, such as those as are described in reference to the figures herebelow.

Reader 310 may include one or more additional components, not shown but selected from the group consisting of: a chamber configured to store multiple probes 350; a reservoir configured to store reference solution 367; and combinations of these.

Figure 6:
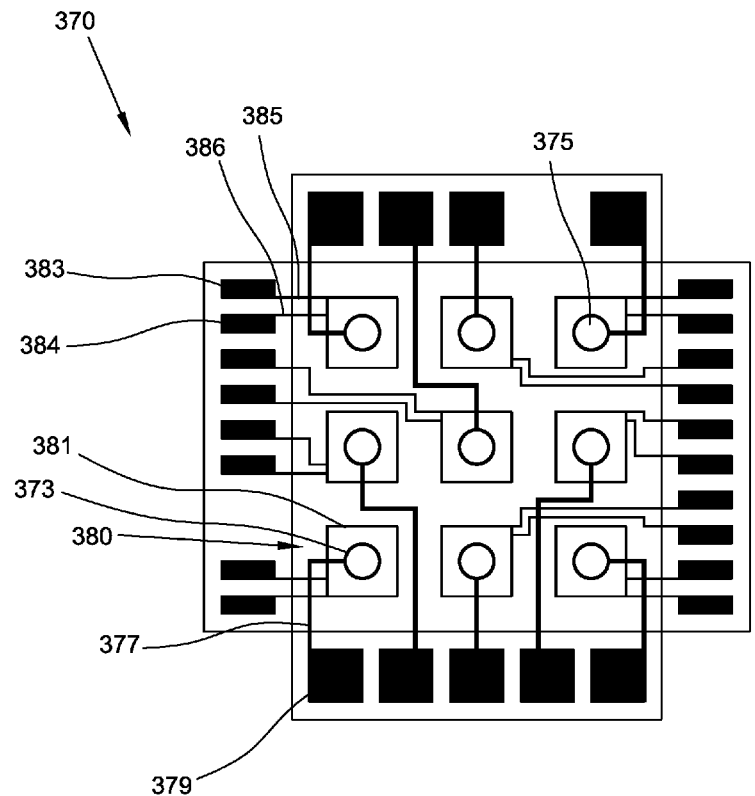
FIG. 6 illustrates a schematic view of an array of sensors.

FIG. 6 illustrates a schematic view of an indicating electrode assembly comprising an array of pH indicating electrodes, according to embodiments of the present invention. Indicating electrode assembly 370 comprises an array of indicating electrodes 375 (a 3 by 3 array as shown in FIG. 6). In an alternative embodiment, one or more indicating electrodes 375 may be configured as a reference electrode. Each electrode 375 is surrounded on an exposed surface by membrane assembly 380. Membrane assembly 380 is configured to cover indicating electrode 375, and to be operably manipulated such as to expose indicating electrode 375 to a sample solution. Operable manipulations include but are not limited to: removal of membrane 381, tearing of membrane 381; separation of membrane 381; and combinations of these. Membrane assembly 380 may be substituted with various other assemblies, such as various other electromechanical assemblies configured to operably provide an opening between a first volume and a second volume. Indicating electrode assembly 370 comprises a multiple layer construction such that conductors, insulators and other functional elements can be assembled to a substrate as is described in reference to FIG. 7 herebelow. One layer comprises electrical traces 377, each terminating at a first end to indicating electrode 375 and at a second end to connection pad 379. In one embodiment, indicating electrodes 375 are fixed to mounting pads 373, and traces 377 are attached to mounting pads 373. Traces 377 and pads 379 are configured to transmit electrical information such as a voltage or other indicating electrode 375 information to a separate device, such as reader 310 of FIG. 5. Another layer of assembly 370 comprises traces 385 and 386, connecting connection pads 383 and 384 to membrane assembly 380. Traces 385 and 386, and connection pads 383 and 384 are configured to provide power (e.g. a positive voltage and ground) to membrane assembly 380. In one embodiment, connection pads 379, 383 and 384 connect to a wire bundle, such as wire bundle 371 of FIG. 5. Traces 377 as well as pads 373 and 379 may be made using a titanium deposition and etching process. All traces may comprise other suitable, electrically conductive materials, such as gold, platinum, copper, aluminum and/or silver. While array 370 is shown with nine indicating electrodes 375, numerous configurations of electrodes may be included such as arrays of ninety or more indicating and/or reference electrodes.

Figure 6A:
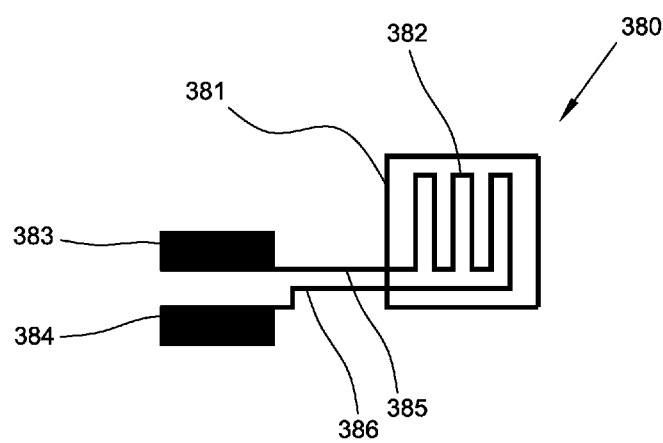
FIG. 6a illustrates a top view of a controllable orifice.

FIG. 6a illustrates a detailed view of an openable membrane assembly, according to embodiments of the present invention. Membrane assembly 380 comprises heating element 382 and membrane 381. Traces 385 and 386 connect electrical connection pads 383 and 384, respectively, to heating element 382. In another embodiment (not shown), multiple membrane assemblies 380 have individual signal pads 383 but share a common ground pad 384', and the triggering of any individual pad 383 causes the connected assembly 380 to rupture. Heating element 382 may be constructed using a gold deposition and etching process, leaving a high resistance pattern configured to generate heat when electrical current is applied. The deposition and etching process may include additional steps and materials, such that heating element 382 is deposited within membrane 381 (e.g. within one or more layers of membrane 381).

In FIG. 6a, heating element 382 is constructed within, in contact with and/or otherwise proximate to membrane 381, such that activation of heating element 382 causes a physical change of membrane 381 such that fluid may pass through membrane 381. This physical change, such as a tear in the membrane caused by thermal forces generated by heating element 382, may allow fluid to enter a previously sealed chamber, as described herebelow in reference to FIG. 7.

Figure 7:
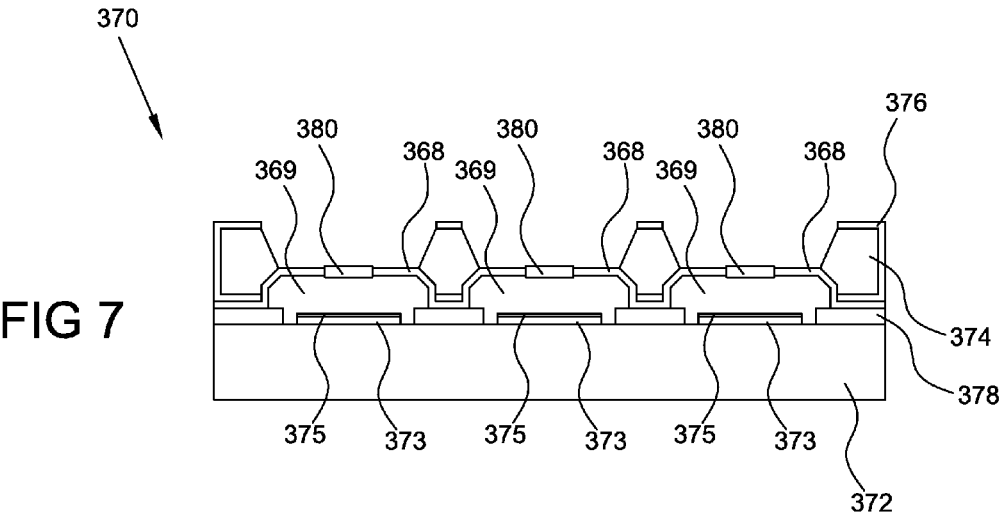
FIG. 7 illustrates a cross sectional view of an array of sensors.

FIG. 7 illustrates a cross sectional view of an array of indicating electrodes included within an indicating electrode assembly, according to embodiments of the present invention. Indicating electrode assembly 370 includes multiple chambers 369, surrounded by walls 378 and cover 368. Cover 368 comprises membrane assembly 380, constructed and arranged to be electronically modified, as described in reference to FIG. 6a hereabove, such as to open chamber 369 to the surrounding environment (e.g. exposure to a sample solution). Indicating electrode assembly 370 also comprises support material 374, surrounded by casing 376. Chambers 369 surround individual indicating electrodes 375, which are each deposited on electrode mounting pads 373. In one embodiment, mounting pads 373 are constructed of titanium, such as titanium deposited in a deposition process. Indicating electrodes 375 typically comprise Iridium Oxide (IrOx) electrodes. Indicating electrodes 375 may also comprise other materials suitable for electrically measuring the pH of a sample solution. The components of indicating electrode assembly 370 are constructed on substrate 372, typically a glass, silicon or plastic substrate. A typical fabrication process for manufacturing indicating electrode assembly 370 is described in detail in reference to FIG. 9 herebelow. While array 370 is shown with three indicating electrodes 375, numerous configurations of electrodes may be included such as arrays of ninety or more indicating and/or reference electrodes, in various square, rectangular and other geometric configurations.

Figure 7A:
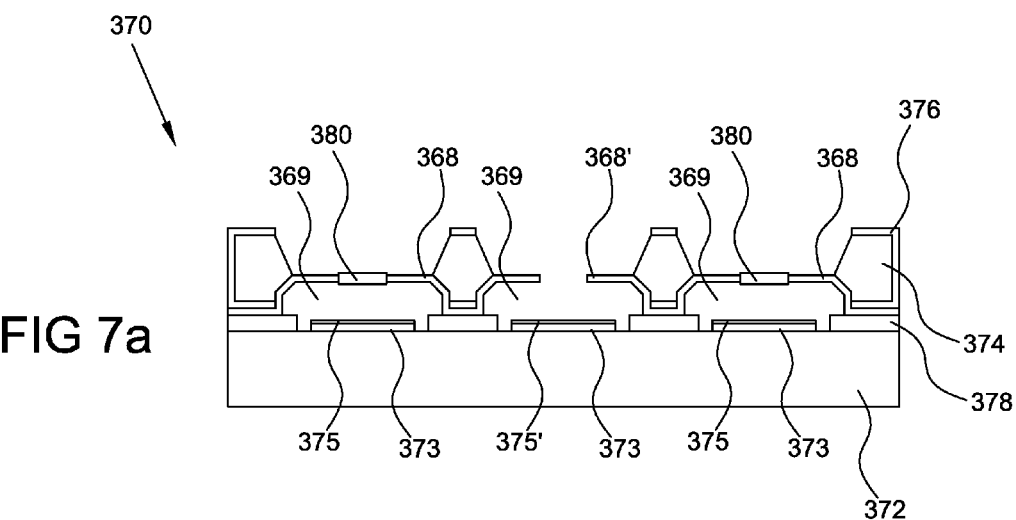
FIG. 7a illustrates a cross sectional view of the array of FIG. 7 after an activation process has occurred.

Referring now to FIG. 7a, membrane assembly 380 of FIG. 7 has been modified, such that an opening in cover 368' is created between chamber 369 and the surrounding environment. After the opening is created and indicating electrode assembly 370 is placed into a sample solution, only the indicating electrode positioned under cover 368' (noted in FIG. 7a as indicating electrode 375') will be exposed to the sample solution. In one embodiment, one or more chambers 369 are constructed as vacuum chambers, such that when membrane assembly 380' (corresponding to cover 368') is modified, the sample solution is drawn into chamber 369. Vacuum chambers are typically created by manufacturing chambers 369 and its surrounding walls in a vacuum environment. Additionally or alternatively, the walls of one or more chambers 369 may be shaped or include one or more coatings (e.g. a hydrophilic coating) such as to draw sample solution into chamber 369. Additionally or alternatively, the wall materials of construction may be hydrophilic or otherwise constructed and arranged to draw sample solution into chamber 369.

Figure 8:
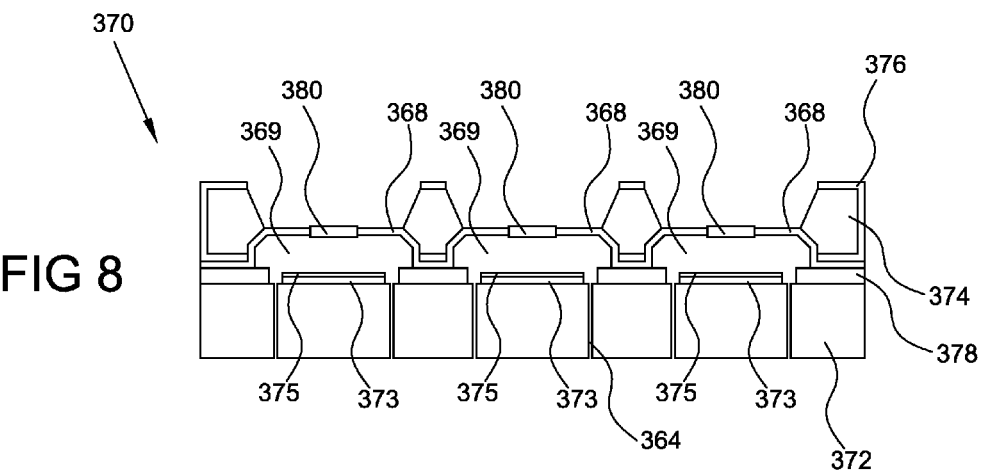
FIG. 8 illustrates a cross sectional view of another embodiment of an array of sensors.

FIG. 8 illustrates an indicating electrode assembly, according to embodiments of the present invention. Indicating electrode assembly 370 is typically constructed and arranged with similar components to indicating electrode assembly 370 of FIGS. 7 and 7a. Indicating electrode assembly 370 of FIG. 8 further includes vents 364, positioned within substrate 372, between chamber 369 and the opposite surface of substrate 372. Vents 364 are configured to improve transfer of sample or other solutions into chambers 369. While array 370 is shown with three indicating electrodes 375, numerous configurations of electrodes may be included such as arrays of ninety or more indicating and/or reference electrodes.

Figure 8A:
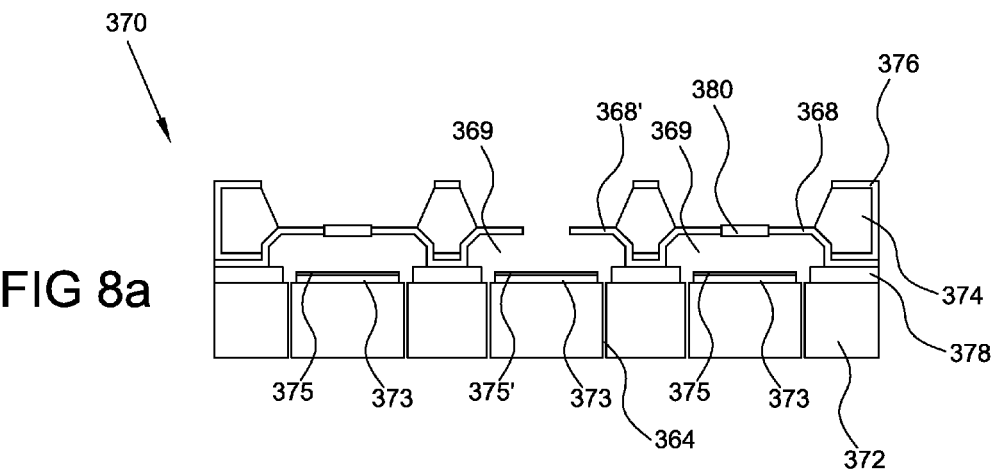
FIG. 8a illustrates a cross sectional view of the array of FIG. 8 after an activation process has occurred.

Referring now to FIG. 8a, membrane assembly 380 of FIG. 8 has been modified, such that cover 368' is opened through manipulation of membrane assembly 380', as has been described in reference to FIG. 7a hereabove. Chamber 369 is now exposed to its surrounding environment, typically including a sample solution. Pressure increases caused by entry of fluid into chamber 369 are alleviated through vents 364. In one embodiment, vents 364 may be operably attached to a negative pressure source, such as a vacuum pump, not shown but configured to draw sample solution into open chamber 369.

Figure 9:
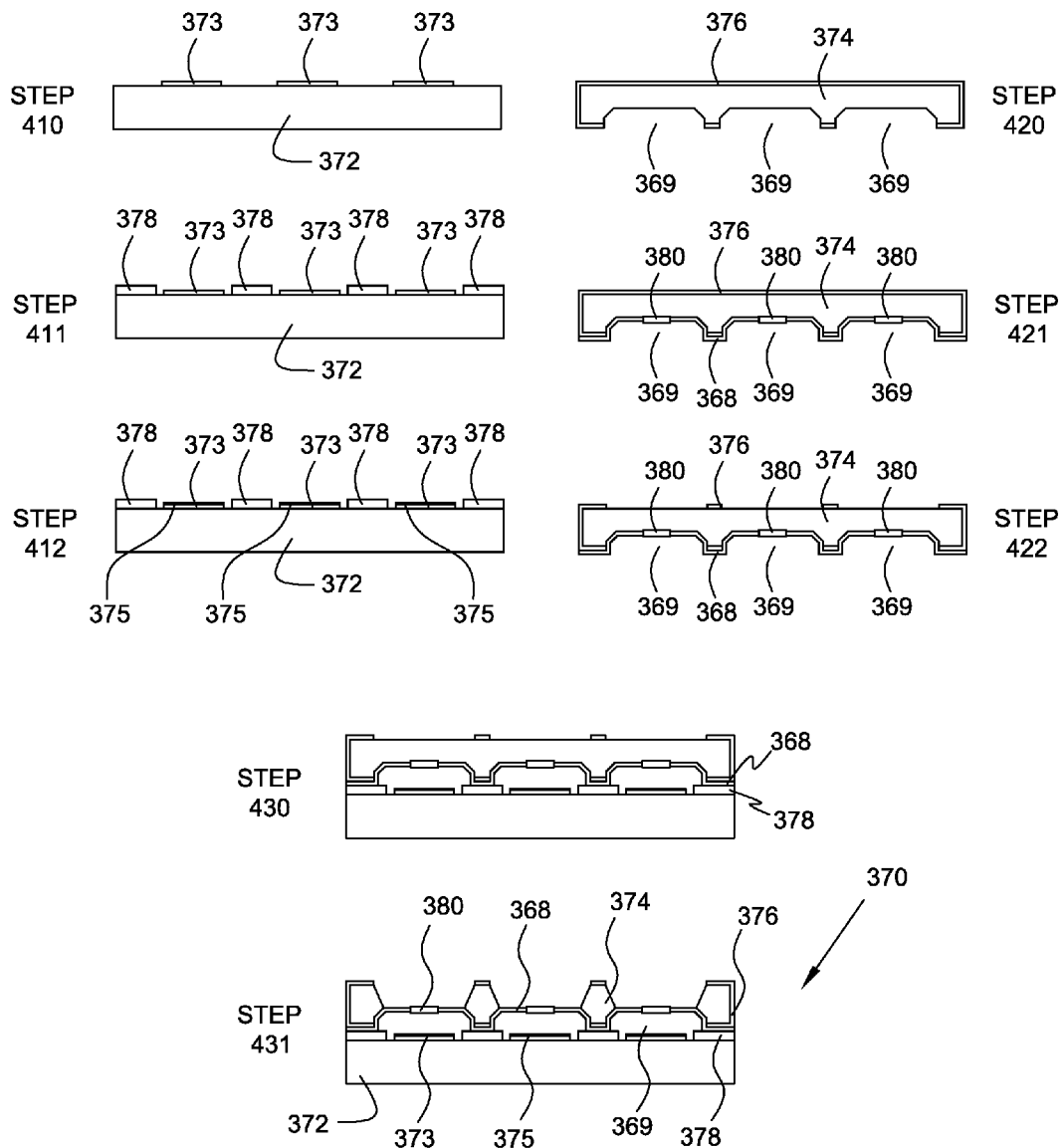
FIG. 9 illustrates a process of manufacturing an array of sensors.

FIG. 9 illustrates a step-wise process of manufacturing an array of indicating electrodes, according to embodiments of the present invention. In a typical embodiment, STEPS 410 through 412 are performed as a sequential group, and STEPS 420 through 422 are performed as a sequential group. STEP 410 shows substrate 372 with titanium mounting pads 373. Mounting pads 373 have been mounted to substrate 372 using a deposition and etching process, creating a patterned layer on substrate 372, typically titanium, typically using an E-beam evaporator and photolithography. Photolithography and etching processes have removed portions of the deposited layer, leaving mounting electrodes 373 as shown.

STEP 411 shows the assembly of STEP 410, including walls 378, typically comprising $SiO_2$. Walls 378 have been deposited onto substrate 372 using a deposition process, followed by a curing and etching process to achieve the configuration shown.

STEP 412 shows the assembly of STEP 411, now including indicating electrodes 375. Electrodes 375 typically comprise an Iridium Oxide pad that has been deposited directly onto mounting electrode 373. After deposition of the electrodes 375, a post fabrication process may be performed, including one or more of a thermal treatment, a voltage treatment (such as a voltage treatment comprising application of a known voltage to the iridium oxide layer in the presence of a buffer solution), or a chemical treatment (e.g., exposure to a chemical solution for a period of time). The voltage is applied for a fixed period of time, in constant or varied levels, in order to modify the chemical composition of the iridium oxide layer. When exposed to a reference solution, this voltage modification can be used to cause the electrode to produce a known voltage response relative to the pH of the reference solution, such as to avoid calibration.

STEP 420 shows support material 374, typically a silicon wafer, having been encapsulated by casing 376, typically a Silicon Nitride casing. Both casing 376 and support material 374 have been etched to create recesses for chambers 369 in support material 374.

STEP 421 shows the assembly of STEP 420, including cover material 368 having been deposited onto casing 376 and chamber 369. Membrane assembly 380 is positioned within cover material 368. Membrane assembly 380 is typically a deposited multi layer assembly, comprising a silicon nitride layer (e.g. a top portion of cover material 368 proximate membrane assembly 380), a layer of gold and chromium configured as a heating element, and a second layer of silicon nitride (e.g. a bottom portion of cover material 368). The two silicon nitride layers of membrane assembly 380 function as a membrane which can be controllably manipulated by the activation of the heating element.

STEP 422 shows the assembly of STEP 421, after an etching process has been performed removing portions of casing 376 that covered the tops of chambers 369.

STEP 430 shows the assemblies of STEPS 412 and 422, bonded together. Cover material 368 has been bonded to walls 378, typically using an anodic or similar bonding process.

STEP 431 shows the final indicating electrode assembly 370. A final wet etching process has been performed removing the support material 374 from above the cover 368, exposing membrane assemblies 380.

While array 370 of FIG. 9 is shown with three indicating electrodes 375, numerous configurations of electrodes may be included such as arrays of ninety or more indicating and/or reference electrodes.

FIG. 10 illustrates a cross sectional view of an alternative embodiment of an array of electrodes, according to the embodiments of the present invention. Array 370' comprises at least one indicating electrode 375 and at least one reference electrode 360'. Indicating electrode 375 is typically constructed and arranged, and includes similar components to one or more of indicating electrodes 375 of FIGS. 6 through 8. Indicating electrode 375 may be manufactured as described in reference to FIG. 9 hereabove.

Reference electrode 360' is configured to provide a reference signal with indicating electrode 375 or another indicating electrode, not shown but integral to array 370. Reference electrode 360' and one or more of its components (e.g. walls, chambers, conductive pads and traces, membrane assemblies, etc) may be manufactured in one or more processes similar to those described in reference to FIG. 9 hereabove.

Reference electrode 360' is typically attached to substrate 372 via a mounting pad, such as titanium mounting pad 373'. A chamber 362 surrounds the surface of electrode 360'. Cover 368 comprises membrane assembly 380', which is positioned between chamber 362 and a second chamber, reservoir 366'. Membrane assembly 380' is configured to be operably manipulated such as to expose reference electrode 360' to reference solution 367. Operable manipulations include but are not limited to: removal of a portion (e.g. a membrane) of membrane assembly 380', tearing of membrane assembly 380'; separation of membrane assembly 380'; and combinations of these. Operable manipulation of a membrane can be accomplished through applications of one or more forces to the membrane. Typical force applications include but are not limited to: activation of a heating element within, on or proximate to the membrane; applying pressure such as reference solution pressure against the membrane; applying pressure such as gas pressure formed by creating a bubble with electrolysis (as discussed in reference to FIG. 3 hereabove) against the membrane; and combinations of these. Membrane assembly 380' may be substituted with various other assemblies, such as various other electromechanical assemblies configured to operably provide an opening between a first area and a second area. Support material 374 surrounds chamber 362 and reservoir 366'. Support material 374 is surrounded by casing 376.

A liquid junction, junction 365' is positioned between chamber 369 and chamber 362. Liquid junction 365' is typically constructed and arranged as described in reference to FIGS. 1 through 5 hereabove. In an alternative embodiment, a virtual liquid junction 365' may be used, as is described in applicants co-pending application, Provisional Application Ser. No. 61/531,546, entitled MEASUREMENT DEVICE WITH READER AND DISPOSABLE PROBE, by Clark et al, filed of even date herewith, the disclosure of which is incorporated herein by reference in its entirety.

Referring now to FIGS. 10a and 10b, typical operation of array 370' of FIG. 10 is illustrated. In FIG. 10a, membrane assembly 380' has been activated, such as via one or more wires, not shown but described in detail in reference to FIGS. 6 and 6a hereabove. Reference solution 367 has entered chamber 362' and is in contact with reference electrode 360' and liquid junction 365'. In FIG. 10b, membrane assembly 380 has been activated, such as via one or more wires as is described hereabove. Sample solution can be brought into contact with indicating electrode 375 and liquid junction 365', such that signals from indicating electrode 375 and reference electrode 360' can be interpreted by a reading device as has been described in reference to FIG. 5 hereabove.

Figure 10C:
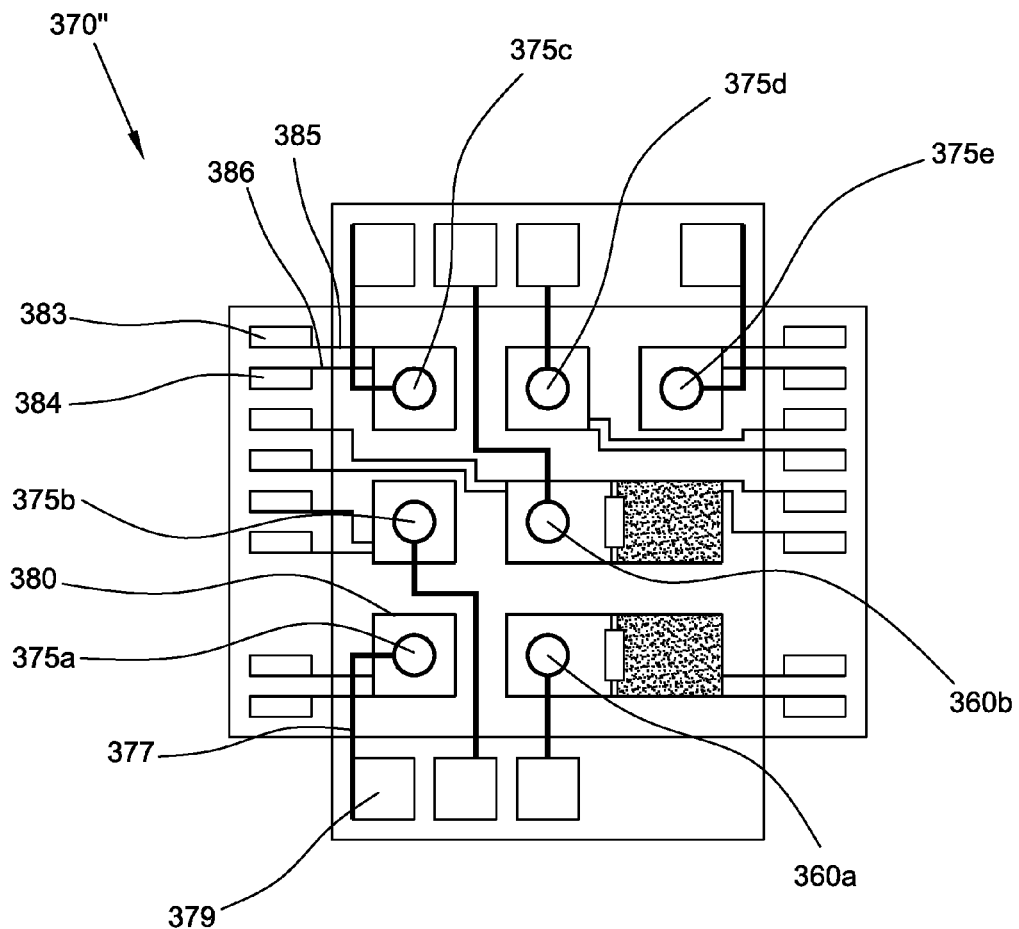
FIG. 10c illustrates a cross sectional view of an array of sensors comprising multiple indicating electrodes and multiple reference electrodes.

While array 370 of FIGS. 10, 10a and 10b is shown with a single indicating electrode 375 and a single reference electrode 360', numerous configurations of electrodes may be included such as arrays of nine or more, thirty ore more, or ninety or more indicating and/or reference electrodes. In FIG. 10c, array 370" comprises two reference electrodes 360a and 360b, and five indicating electrodes 375a through 375e. In a typical embodiment, a single reference electrode 360a or 360b is configured to perform multiple readings, such as to provide a reference to multiple indicating electrodes 375a through 375e.

As shown in FIG. 10c, array 370" can include one layer comprising electrical traces 377, each terminating at a first end to indicating electrodes 375a and 375b and at a second end to connection pad 379. In one embodiment, indicating electrodes 375a and 375b are fixed to mounting pads 373, and traces 377 are attached to mounting pads 373 (mounting pads 373 not shown, but positioned directly beneath the electrodes, as shown in FIGS. 10, 10a, and 10b hereabove). Traces 377 and pads 379 are configured to transmit electrical information such as a voltage or other indicating electrode information to a separate device, such as reader 310 of FIG. 5. Another layer of assembly 370" comprises traces 385 and 386, connecting connection pads 383 and 384 to membrane assembly 380. Traces 385 and 386, and connection pads 383 and 384 are configured to provide power (e.g. a positive voltage and ground) to membrane assembly 380. In one embodiment, connection pads 379, 383 and 384 connect to a wire bundle, such as wire bundle 371 of FIG. 5. Traces 377 as well as pads 373 and 379 may be made using a titanium deposition and etching process. All traces may comprise other suitable, electrically conductive materials, such as gold, platinum, copper, aluminum and/or silver. While array 370" is shown with five indicating electrodes 375a-e, numerous configurations of electrodes may be included such as arrays of ninety or more indicating and/or reference electrodes.

The foregoing description and accompanying drawings set forth a number of examples of representative embodiments at the present time. Various modifications, additions and alternative designs will become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

What is claimed is:

1. A system for obtaining a pH measurement of a sample comprising:
   a disposable probe comprising:
   a first chamber storing a reference solution;
   a second chamber housing a reference electrode;

a third chamber surrounding an indicating electrode configured to be exposed to the sample, wherein the third chamber comprises a first orifice configured to be opened so as to expose the indicating electrode to the sample; and a second orifice positioned between the first and second chambers, the second orifice configured to be opened so as to expose the reference solution to the reference electrode.

2. The system of claim 1 further comprising an electronics module constructed and arranged to activate at least one orifice.

3. The system of claim 2 wherein the electronics module comprises a lookup table that comprises orifice activation information.

4. The system of claim 2 comprising multiple electrodes configured to be exposed to the sample, and wherein the electronics module is constructed and arranged to allow an operator to individually activate each electrode in the multiple electrodes.

5. The system of claim 1 wherein at least one orifice comprises a membrane.

6. The system of claim 5 wherein the membrane comprises a multi-layer membrane.

7. The system of claim 5 wherein the membrane comprises a heating element constructed and arranged to create an opening in the membrane.

8. The system of claim 7 wherein at least a portion of the heating element is positioned in contact with the membrane.

9. The system of claim 1 wherein the at least one electrode comprises an iridium oxide electrode.

10. The system of claim 1 wherein the at least one electrode is manufactured using a MEMS process.

11. The system of claim 1 further comprising a liquid junction.

12. The system of claim 1 further comprising a substrate, and wherein the at least one electrode is positioned on and/or proximate to the substrate.

13. The system of claim 1 further comprising a reader constructed and arranged to operably engage with the disposable probe and provide pH information of the sample.

14. The system of claim 1 wherein each of the second and third chamber comprises a vacuum chamber constructed and arranged to draw a solution into the chamber.

15. The system of claim 1 wherein the first chamber is a fluidic closed loop channel.

16. A disposable probe comprising:
a first chamber storing a reference solution;
a second chamber housing a reference electrode;
a third chamber surrounding an indicating electrode configured to be exposed to a sample, wherein the third chamber comprises a first orifice configured to be opened so as to expose the indicating electrode to the sample; and
a second orifice positioned between the first and second chambers, the second assembly configured to be opened so as to expose the reference solution to the reference electrode.

17. The disposable probe of claim 16 wherein each of the first and second assembly comprises a membrane.

* * * * *